US009308072B2

(12) United States Patent
Balar

(10) Patent No.: US 9,308,072 B2
(45) Date of Patent: Apr. 12, 2016

(54) BIOMEDICAL FILTER

(76) Inventor: Nilesh Balar, Cresskill, NJ (US)

(*) Notice: Subject to any disclaimer, the term of this patent is extended or adjusted under 35 U.S.C. 154(b) by 1656 days.

(21) Appl. No.: 12/385,663

(22) Filed: Apr. 15, 2009

(65) Prior Publication Data

US 2010/0268262 A1    Oct. 21, 2010

(51) Int. Cl.
*A61F 2/01* (2006.01)
(52) U.S. Cl.
CPC .............. *A61F 2/01* (2013.01); *A61F 2002/016* (2013.01); *A61F 2210/0004* (2013.01); *A61F 2230/006* (2013.01); *A61F 2230/0008* (2013.01); *A61F 2230/0067* (2013.01); *A61F 2250/0035* (2013.01); *A61F 2250/0067* (2013.01)

(58) Field of Classification Search
USPC .......................................................... 606/200
See application file for complete search history.

(56) References Cited

U.S. PATENT DOCUMENTS

| 3,868,956 | A | 3/1975 | Alfidi | |
| 4,425,908 | A | 1/1984 | Simon | |
| 4,886,062 | A | 12/1989 | Wiktor | |
| 5,569,295 | A | 10/1996 | Lam | |
| 5,709,704 | A * | 1/1998 | Nott et al. | 606/200 |
| 6,972,025 | B2 | 12/2005 | WasDyke | |
| 7,229,471 | B2 | 6/2007 | Gale et al. | |
| 7,347,869 | B2 | 3/2008 | Hojeibane | |
| 7,498,385 | B2 | 3/2009 | Swetlin et al. | |
| 2007/0203520 | A1 * | 8/2007 | Griffin et al. | 606/200 |
| 2007/0219626 | A1 | 9/2007 | Rolano | |
| 2007/0250158 | A1 | 10/2007 | Krivoruchko et al. | |
| 2008/0015683 | A1 | 1/2008 | Kramer-Brown | |
| 2008/0027481 | A1 | 1/2008 | Gilson et al. | |
| 2008/0281350 | A1 | 11/2008 | Sepetka et al. | |

FOREIGN PATENT DOCUMENTS

WO    WO2007/079413    7/2007

* cited by examiner

*Primary Examiner* — Ryan J Severson
*Assistant Examiner* — Anh Dang
(74) *Attorney, Agent, or Firm* — Chandrakant Shroff

(57) ABSTRACT

A drug-eluting medical filter having a conically shaped wire frame with a circular base and a plurality of bioabsorbable prongs extending at various positions around the periphery of the base toward a common apex. The prongs have a variable thickness along their length and contain bioactive material, such as heparin or other anti-platelet agent, etc. The bioactive material is varied in concentration along the length of the prongs depending on the need by the patient, and a protective or other coating can be applied on any portion of the frame and/or prongs.

8 Claims, 5 Drawing Sheets

BIOMEDICAL FILTER

BACKGROUND OF THE INVENTION

Insertable medical devices used as vascular supports (i.e., stents) or filters have been used in various medical procedures, such as in angioplasty. An example of an intravascular radially expandable stent used in angioplasty is described in U.S. Pat. No. 4,886,062 issued to Wiktor on Dec. 12, 1989. This device includes a wire winding having the shape of a helical spring, see the front page drawing. U.S. Pat. No. 3,868,956 issued to Alfidi et al. on Mar. 4, 1975 shows a vessel implantable device made of a biocompatible shape memory nickel-titanium alloy wire (i.e., Nitinol wire).

In particular, biomedical filters are implanted in veins to capture emboli or thrombi. For example, prior to surgery, a filter can be implanted into the inferior vena cava to protect the heart and lungs from clots. US Published Application No. 2008/0027481 filed by Gilson et al., published Jan. 31, 2008 describes a generally conically shaped vascular filter that appears to include a Nitinol frame structure with at least a portion of it including bioabsorbable material, see paragraphs 27-33. The filter can include barbs, see 302, FIGS. 26(a) and (b). The filter catches thromboemboli in the inferior vena cava as the blood travels toward the heart and lungs.

International patent application WO2007/079413 (Kashkarov et al.) describes an embolus blood clot filter with bioresorbable coated filter members, see front page drawing, having a structure generally corresponding to current description, including bioabsorbable portions extending from substrate structure (e.g., Nitinol substrate). However, this document appears to be silent regarding gradually thickening bioabsorbable and/or bioactive prong elements as in the present inventive device.

U.S. Pat. No. 6,972,025 issued to WasDyke on Dec. 6, 2005 describes an intravascular filter with a bioabsorbable centering element, see abstract. Similarly, see U.S. Pat. No. 7,491,215 issued to Vale et al.

U.S. Pat. No. 7,347,869 issued to Hojeibane et al. on Mar. 25, 2008 describes an implantable valvular prosthesis including Nitinol and bioabsorbable material. However, this document appears to be silent regarding the particular relationship of the bioabsorbable extensions of the barbs and filter structure that are attached to the Nitinol portions.

U.S. Pat. No. 7,229,471 issued to Gale et al. on Jun. 12, 2007 describes compositions containing fast-leaching plasticizers for use in medical devices, e.g., bioabsorbable materials. However, this document appears to be silent regarding the particular filter and/or stent structure.

U.S. Pat. No. 5,569,295 issued to Lam on Oct. 29, 1996 describes expandable stents that include superelastic NiTi alloys (column 7, second full paragraph) and use of bioabsorbable adhesives, column 2, lines 44-47.

US Patent Application No. 2008/0281350 filed by Srpetka et al. describes aneurysm occluding devices using a biocompatible matrix, including shape memory plastics.

U.S. Pat. No. 4,425,908 issued to Simon on Jan. 17, 1984 describes a blood clot filter placeable in a vein, e.g., vena cava, including Nitinol wires, see passage in document under "Detailed Description". However, this document appears to be silent regarding the use of varying-thickness bioabsorbable material and the structure of the present inventive device.

U.S. Pat. No. 7,498,385 issued to Swetlin et al. describes a polyester composition that can be used to make a biocompatible stent or other biomedical structure.

US Patent Application No. 2007/0250158 to Krivoruchko et al. describes a laminated stent including a metal coating, see the abstract. Also, related WO 2007127541.

US Patent Application No. 2008/0015683 to Kramer-Brown describes a stent made of cobalt chromium alloy.

US Patent Application No. 2007/0219626 to Rolando describes a stent including bioabsorbable material.

However, it is noted that none of the documents uncovered and cited below appear to describe the combination of the Nitinol ring-frame substrate with gradually thickening prong extensions and the bioabsorbable extensions on the Nitinol prongs as described herein.

The cited documents all appear to be directed to devices and structures that can be placed in anatomic vessels, e.g., veins and arteries, and which have either shape memory (e.g., cobalt chromium), metal or nonmetal coating, and/or bioabsorbable features, or general arrangements for applying a coating onto a medical device that corresponds to the inventive filter or stent device.

However, none of the known structures provide a structure that controls the rate of release of a bioactive material after implantation of the device, e.g., by catheter, in a predetermined manner using a plurality of conically shaped bioabsorbable prongs as herein described.

Therefore, there is a need for an implantable vascular medical device in which a bioactive substance, e.g., heparin or other anti-platelet drug, etc., is released at a predetermined, controlled, varying rate after implantation, that is based on the particular needs of a patient. This is achieved in the inventive device by the particular construction of bioabsorbable prongs containing the bioactive material, with optional additional coatings, on an expandable wire frame that includes an undulating ring core and a plurality of transversely attached wire segments. The wire frame can be Nitinol or any other biocompatible shape-memory metal or alloy material, or a comparable biocompatible polymer shape-memory material.

BRIEF SUMMARY OF THE INVENTION AND OBJECTIVES

It is an object of the present invention to provide a biomedical filter having a wire frame including an undulating wire ring, that includes a plurality of prong segments attached in a spaced arrangement along the perimeter of and generally coaxially oriented with respect to the axis of the wire ring; and having a plurality of bioactive agent-containing bioabsorbable prongs projecting from respective wire segments.

It is a further object to provide the above medical device in which the bioabsorbable prongs vary in thickness along their length and contain a predetermined varying amount of an eluting drug or other bioactive agent that elutes at a predetermined rate after implantation.

It is a yet further objective to provide the above biomedical filter in which the bioabsorbable prongs decrease in thickness from a base end where the prong is attached to a respective prong segment, towards the apex, particularly forming conical shapes.

BRIEF DESCRIPTION OF THE DRAWINGS

FIG. 5 shows a perspective view of a stent configuration, to which an implanted filter converts after a given period of time, when the bioabsorbable material has been substantially resorbed.

DETAILED DESCRIPTION

Figure 1:
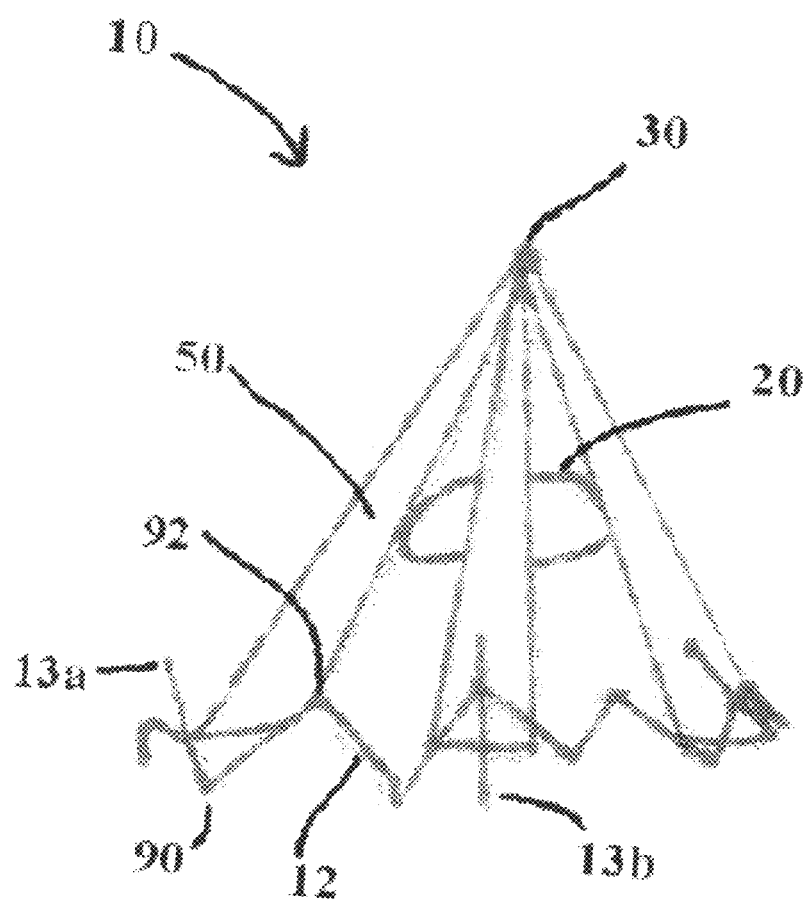
FIG. 1 shows a perspective view of a filter according to one embodiment of the invention.

FIG. 1 shows a perspective view of a medical filter 10, according to one embodiment of the invention. The filter has a wire frame that has a generally undulating circular ring 12, with a plurality of short wire prong segments (13a and 13b) attached to and around the periphery of the undulating ring, such as by soldering, welding or adhesive bonding, all of which are well known in the art. The individual wire prong segments (13a and 13b) each have a longitudinal axis that is oriented along a direction that is transverse with respect to the outer periphery of the ring.

Some of the wire segments can be oriented to act as hooks or barbs 13a, FIG. 1, that allow the device to be held in place to surrounding tissue after the device is implanted, such as by using a catheter, for insertion into a blood vessel. The remaining wire segments act as support anchors 13b for the bases of a respective plurality of bioabsorbable prongs 50.

A bioabsorbable ring 20 is positioned between the ring frame and the apex of the filter, to hold the bioabsorbable prongs in a conical arrangement as shown. After the bioabsorbable ring has been resorbed into the surrounding tissue, the prongs may expand to form a stent arrangement as described in relation to FIG. 5, below. The bioabsorbable ring can be attached to the bioabsorbable prongs either inside the conical structure or outside, using a bioabsorbable adhesive or any other manner of attaching.

Figure 2:
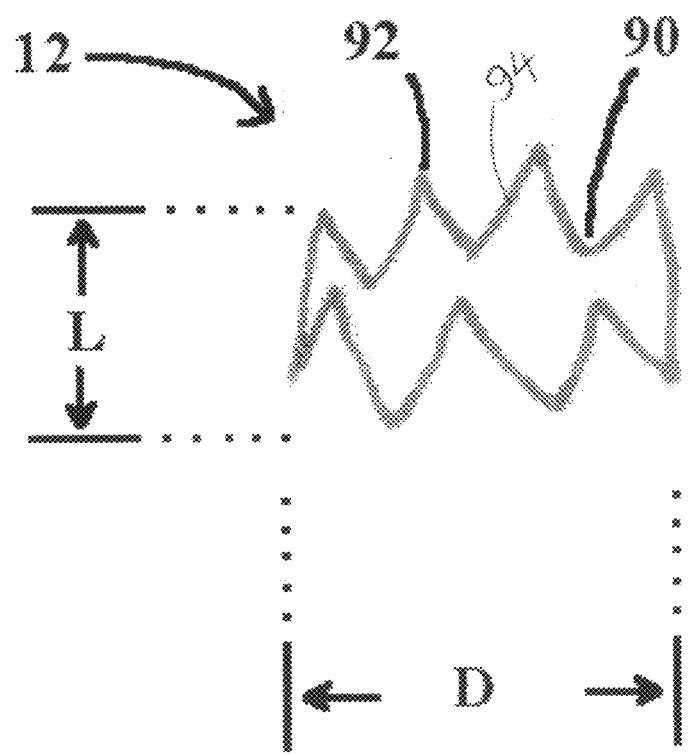
FIG. 2 shows a perspective view of the wire frame core (item 12) of FIG. 1.

As shown in FIG. 2, the wire frame has a generally ring-shape arrangement with various undulations around its perimeter that can be generally described as a series of apices, i.e., "peaks" 92 and "valleys" 90, distributed around the circumference of the frame 12. Each neighboring peak and valley is connected with a respective strut segment 94. The wire prong segments are attached to the peaks and/or valleys in a manner that depends on factors such as particular site of implant and type(s) of bioactive agents used, e.g., the number of prongs and their angle with respect to the ring frame.

During initial manufacture, the ring frame is formed into the undulating shape and diameter that corresponds to the arrangement required after the device is implanted. This shape is "remembered" by the frame. Immediately prior to and during implantation, the structure is compressed to allow it to be implanted. After implantation, the warmth of the surrounding tissue and blood causes the wire frame to expand to its original "remembered" shape. Simultaneously, the wire prong segments pierce the inside of the surrounding vessel walls.

For Nitinol wire frames, this "remembered" shape is an austenitic crystal arrangement that is formed by annealing in the intended final shape at elevated temperatures. When cooled, the Nitinol converts into a generally pliable martensite crystal arrangement, and the frame structure can then be easily compressed or bent for implantation. After implantation, the warmth of the surrounding tissue causes the frame to revert to its austenitic crystal arrangement and expands to its original shape.

The metal alloy or polymer used in the ring frame is preferably a one-way shape memory material that reverts to its final permanent form after implantation. Alternatively, the material can be superelastic, but must be capable of remaining permanently in the intended final shape after implantation. The material for the ring frame must also be biocompatible or be coated with a biocompatible coating.

The ring 12 can have a diameter D that ranges generally between 28-32 mm depending on factors, such as the patient's medical condition and the maximum extent of expansion required after insertion into the body, for the filter to be held in place by the surrounding tissue, e.g., the inside surface of a blood vessel. The length L is similarly dependent on various medical and practical factors, and can range from several millimeters to about 50 mm. The frame wire can have a thickness of 0.05-0.5 mm.

The wire segments appear as straight segments in the drawings, but can have arcuate shapes to alter the collection area for thromboemboli that enter the filter.

Figure 3:
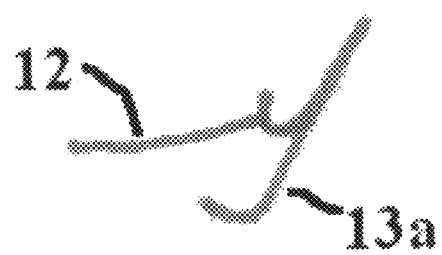
FIG. 3 shows a close-up elevation/cross-sectional view of a portion of the wire frame of FIG. 1, including an attached hook or barb, i.e., wire prongs.
Figure 4:
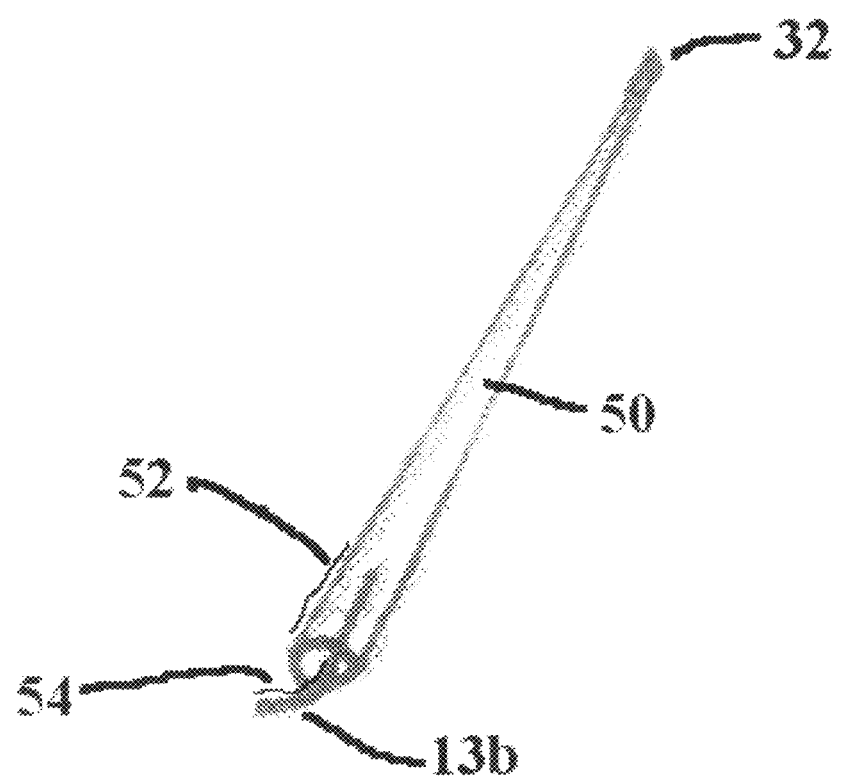
FIG. 4 shows a close-up elevational/cross-sectional view of a protrusion on a portion of the wire frame, including a biodegradable or bioactive coating with varying thickness along and away from the tip of the protrusion.
Figure 8:
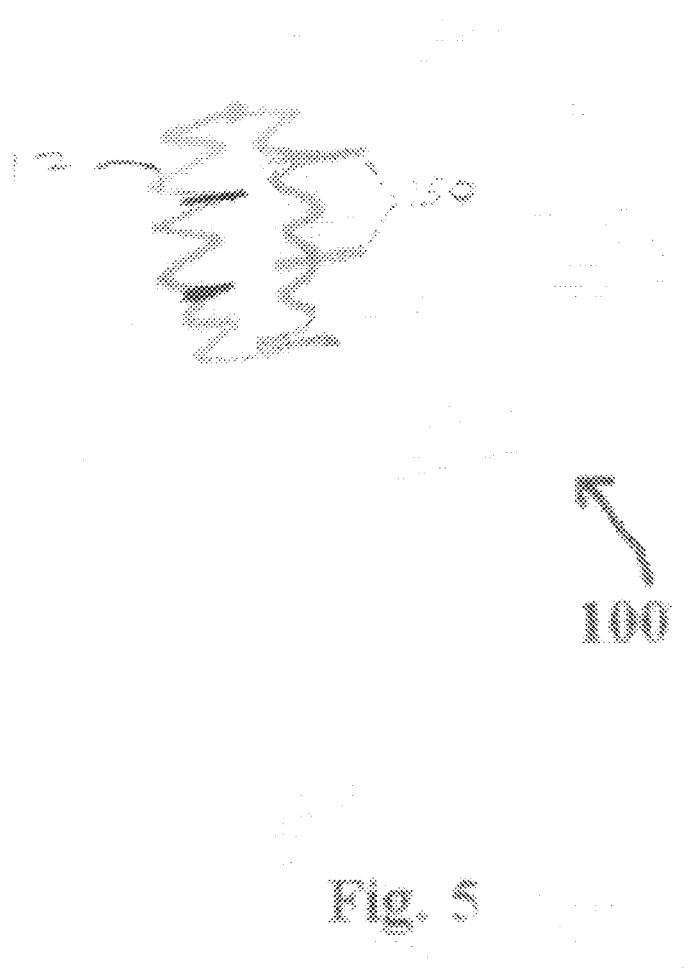

FIG. 3 shows a hook or barb 13a attached to the ring 12 in an orientation that ensures that the hook will enter the surrounding tissue wall after implantation. FIG. 4 shows a wire segment 13b with an attached bioabsorbable prong 50. The bioabsorbable prongs 50, FIG. 4, have a thickness that varies from the base where they are attached to the respective wire segments 13b, to their tips, 32. The bioabsorbable prongs also contain a bioactive material dispersed throughout the bioabsorbable matrix in a manner that ensures that it is eluted in a controlled manner over a period of time. The bioabsorbable matrix can include the bioactive material in any of various arrangements, such as being mixed into the matrix or in a layered arrangement.

An additional optional coating, such as a protective biocompatible coating, can be applied to any portion of the bioabsorbable prongs (e.g., 52) or to the wire ring or segments (e.g., 54).

Examples of types of bioactive agents that can be contained in the bioabsorbable prongs include anti-platelet drugs, such as heparin. Examples of the bioabsorbable materials that can be used to make the prongs can include polyhyroxybutyrate, polycaprolactones, or various copolymers of caprolactone and glycolides, which are well known in the art. The bioactive agent can be added to the bioabsorbable material by mixing the materials together and then forming the prongs, or by coating bioabsorbable prongs with a bioactive agent.

The ring and segments that make up the wire frame are preferably a thin self-expandable, flexible metal such as Nitinol or cobalt-chromium alloy wire. During implantation, such as by using a catheter, the device is compressed into a compact shape, and after implantation, the ring expands until the device is attached to the surrounding tissue and held in place.

In the embodiment shown in FIG. 1, all of the tips of the bioabsorbable prongs meet at a common apex 30 to form a biomedical filter. Alternatively, in the second embodiment of the device 100, shown in FIG. 5, all of the wire prongs 150 extend from the ring frame and are generally oriented in a colinear arrangement. This arrangement occurs after implantation and after all of the bioabsorbable material has been resorbed into the surrounding tissue, leaving behind the non-absorbable metal alloy frame.

In addition, if the ring frame and the plurality of wire prong segments are all made of bioabsorbable shape memory polymer material, the entire structure can be resorbed after a sufficiently long period of time, well beyond the time needed for the bioactive agent to have completely eluted.

For a biomedical filter having a final 3.0 mm diameter ring frame (i.e., the final size after implantation), the wire prongs can be 2-5 mm in length, with bioabsorbable conical prongs attached to 0.5 to 2.0 mm of the end of the respective wire prongs. The bioabsorbable material can contain Heparin having 12-15 kDa length preparation, dispersed throughout the bioabsorbable matrix. The Heparin can be present in an amount sufficient to elute 1-2 units dose per day of Heparin over a time period of weeks or months, depending on the particular bioabsorbable material used. The Heparin can be combined with the bioabsorbable matrix in any suitable manner, such as by thoroughly mixing, and then molding the prongs onto the wire prongs. Alternatively, the Heparin can be present in a layered or other arrangement in the matrix. The Heparin can be combined with the matrix using any suitable process that ensures the steady elution of the Heparin over a given period of time.

The amount of the bioactive agent, e.g. Heparin, the dimensions of the bioabsorbable prongs, and the number of prongs, depend on factors related to the needs and characteristics of the patient and the condition of the patient, and types of medical procedures needed to be performed, including surgery.

I claim:

1. A biomedical filter comprising:
a wire frame including an undulating ring having a plurality of alternating struts and apices;
a plurality of wire segments, spaced around and attached to the periphery of the ring and oriented in a direction such that one end of each of the segments points to a common apical point;
a plurality of projecting substantially conically shaped prongs made of a bioabsorbable matrix material, each prong having a base attached to a respective wire segment and each having a distal tip;
at least a portion of each prong including a bioactive material contained within at least a portion of the prong matrix,
wherein each prong increases continuously in thickness in a substantially linear manner along the entire length of each prong, such that each individual prong structure conforms substantially to a conical shape,
wherein after the filter is implanted, the bioactive material elutes at a predetermined rate that is dependent on the dimensions and number of prongs and the concentration profiles of the bioactive material within the matrix material of the prongs.

2. The device according to claim 1 wherein the wire frame and the segments are made of a shape memory material including shape memory alloys or shape memory polymers.

3. The device according to claim 1 wherein the wire frame and the wire segments have a thickness of 0.1 to 0.5 mm and the ring has an implanted diameter of 28 to 30 mm.

4. The device according to claim 1 wherein the filter is an inferior vena cava filter and the bioactive agent is Heparin.

5. The device according to claim 1, further comprising at least one bioabsorbable ring attached to the prongs at a position between the base and an apex of the bioabsorbable prongs.

6. The device of any of claims 1, 2, 3, 4 or 5 including a protective biocompatible coating on all or any portion of: the wire frame, the wire segments and the bioabsorbable prongs.

7. The device of claim 1 wherein each bioabsorbable prong is separately molded from a bioabsorbable material in the form of a generally conically shaped matrix wherein the matrix at least partially contains the bioactive material within the matrix.

8. The device of claim 7 wherein the bioactive material is Heparin.

* * * * *